(12) United States Patent
Srivastava

(10) Patent No.: US 12,303,484 B2
(45) Date of Patent: May 20, 2025

(54) METHOD OF TREATING CANCER

(71) Applicant: University of Louisiana at Lafayette, Lafayette, LA (US)

(72) Inventor: Radhey Srivastava, Youngsville, LA (US)

(73) Assignee: University of Louisiana at Lafayette, Lafayette, LA (US)

( * ) Notice: Subject to any disclaimer, the term of this patent is extended or adjusted under 35 U.S.C. 154(b) by 894 days.

(21) Appl. No.: 17/237,137

(22) Filed: Apr. 22, 2021

(65) Prior Publication Data

US 2021/0236454 A1     Aug. 5, 2021

Related U.S. Application Data

(63) Continuation-in-part of application No. 16/943,323, filed on Jul. 30, 2020, now abandoned.

(60) Provisional application No. 62/880,726, filed on Jul. 31, 2019.

(51) Int. Cl.
*A61K 31/28* (2006.01)
*A61P 35/00* (2006.01)

(52) U.S. Cl.
CPC .............. *A61K 31/28* (2013.01); *A61P 35/00* (2018.01)

(58) Field of Classification Search
None
See application file for complete search history.

(56) References Cited

U.S. PATENT DOCUMENTS 4,843,069 A * 6/1989 Keller ................. C07F 15/0053
546/4

OTHER PUBLICATIONS

Pacor et al. "Antitumor Action of mer-trichlorobis (dimethylsulphoxide) aminoruthenium (III) (BBR2382) in Mice Bearing Lewis Lung Carcinoma". Metal Ions in Biology and Medicine. 1990, p. 482-484. (Year: 1990).*
Kellar et al. ("Preclinical Murine Models for Lung Cancer: Clinical Trial Applications". BioMed Research International. May 2015; Article ID 621324. pp. 1-17. (Year: 2015).*
David et al. "Synthesis, Characterization, and Anticancer Activity of Ruthenium-Pyrazole Complexes". Journal of Inorganic Biochemistry. 2012; 111:33-39. (Year: 2012).*
Holliday et al. "Choosing the Right Cell Line for Breast Cancer Research". Breast Cancer Research. 2011; 13:215. (Year: 2011).*

* cited by examiner

*Primary Examiner* — Leslie A. Royds Draper
(74) *Attorney, Agent, or Firm* — Kean Miller LLP; Jessica C. Engler; Brian J. Servé

(57) ABSTRACT

Disclosed herein is a method of treating patients with NSCLC subtypes of cancer by reducing tumor burden, comprising administering at least one dose of purified Ruthenium (III) Pyrazole complexes to patients suffering from NSCLC, wherein said dose is therapeutically sufficient. In one or more embodiments, the Ruthenium III Pyrazole is $RuCl_3(DMSO)(dmPyz)_2$.

3 Claims, 5 Drawing Sheets

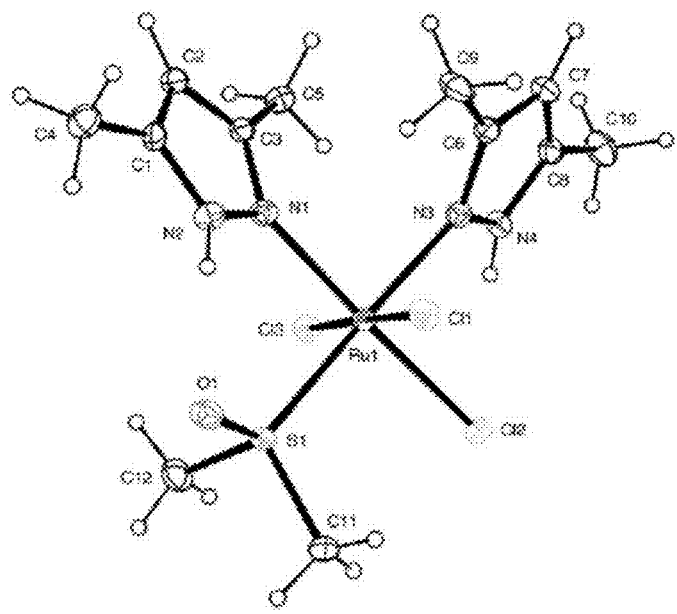
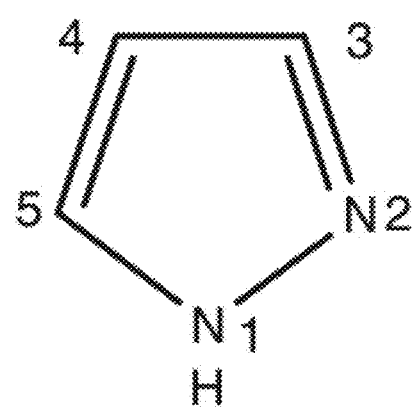
Figure 2. Structure of a Pyrazole.

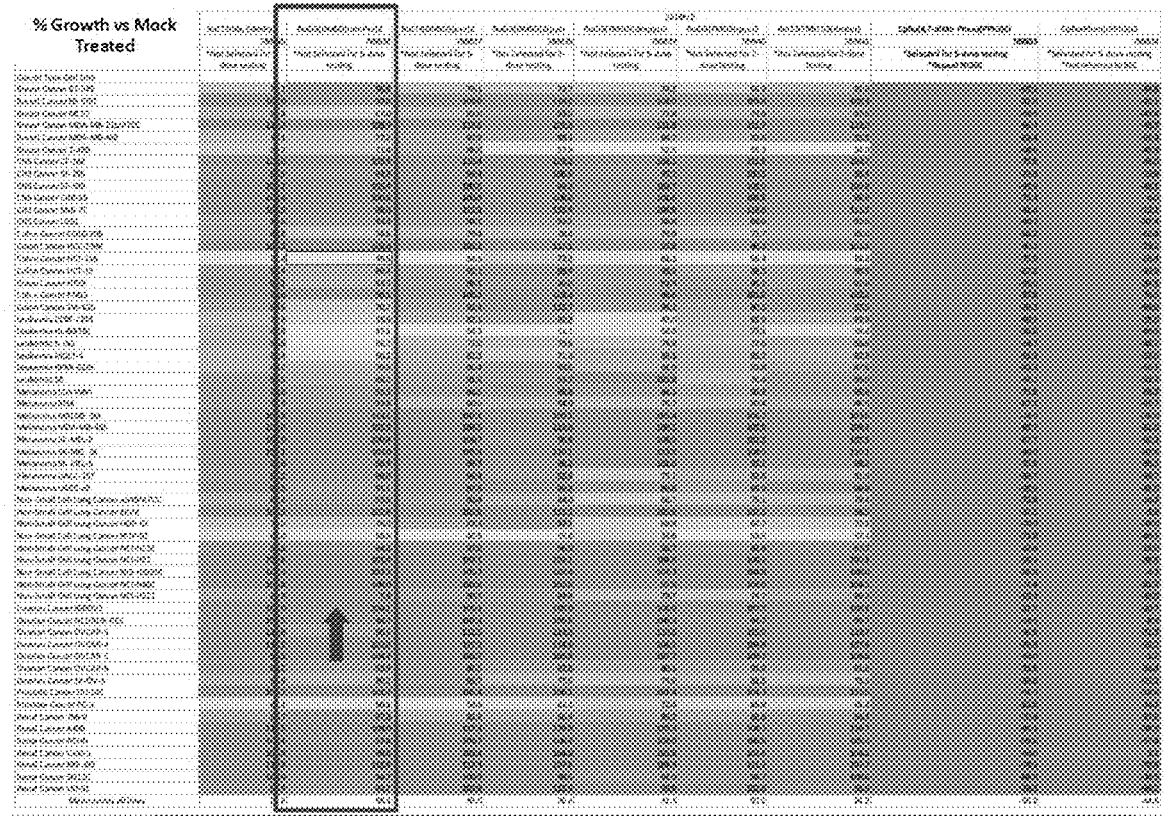
Figure 3.
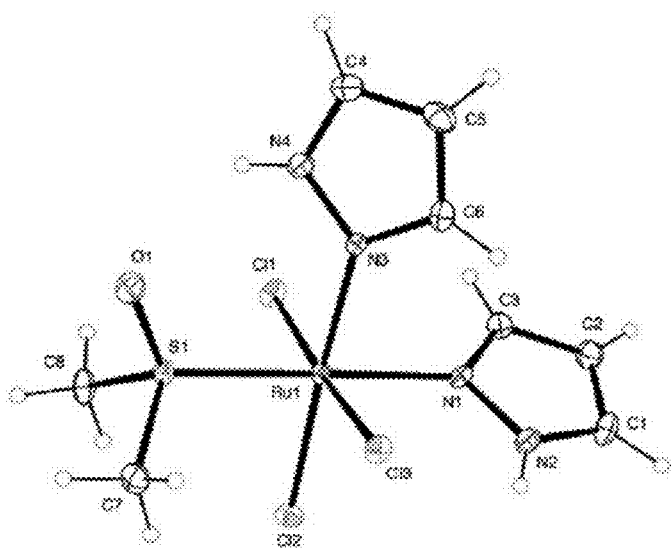
Fig. 4. Ortep diagram of mer-[RuCl₃(DMSO)(pyz)₂]

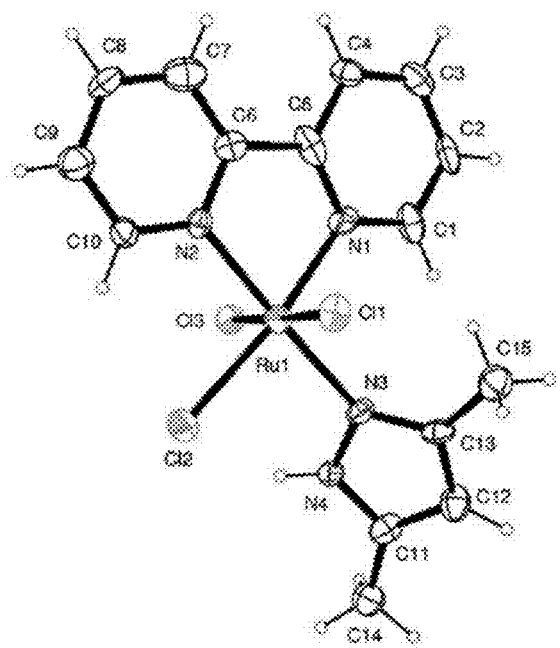
Fig. 5. Ortep diagram of mer-[RuCl₃(bpy)(dmpyz)] 3.
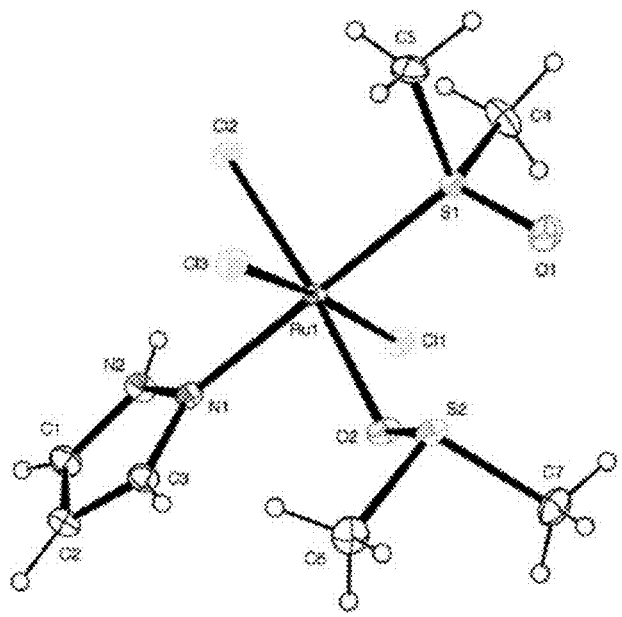
Fig. 6. Ortep diagram of mer-[RuCl₃(DMSO)₂(pyz)] 2.

—◆—24 hrs treatment
—■—48 hrs treatment
—▲—72 hrs treatment

—◆—24 hrs treatment
—■—48 hrs treatment
—▲—72 hrs treatment

METHOD OF TREATING CANCER

CROSS REFERENCE TO RELATED APPLICATIONS

This application is a Continuation in Part of U.S. patent application Ser. No. 16/943,323, entitled "METHOD OF TREATING CANCER", filed Jul. 30, 2020, which claims benefit to the U.S. Provisional Patent Application No. 62/880,726, entitled "METHOD OF TREATING CANCER", filed Jul. 31, 2019.

STATEMENT REGARDING FEDERALLY SPONSORED RESEARCH OR DEVELOPMENT

Not Applicable.

REFERENCE TO A "SEQUENCE LISTING," A TABLE, OR A COMPUTER PROGRAM

Table 1 presents effective Dose 50 (ED50) values of drug mer-[RuCl$_3$(DMSO)(dmpyz)$_2$ on Lung Cancer cell lines at different treatment duration.

DESCRIPTION OF THE DRAWINGS

FIG. 1 is an Ortep diagram of mer-[RuCl$_3$(DMSO)(dmpyz)$_2$.

FIG. 2 is the structure of a pyrazole.

FIG. 3 is a table showing test results for Ruthenium complexes as anticancer agent.

FIG. 4 is an Ortep diagram of mer-[RuCl$_3$(DMSO)(pyz)$_2$].

FIG. 5 is an Ortep diagram of mer-[RuCl$_3$(bpy)(dmpyz)$_2$].

FIG. 6 is an Ortep diagram of mer-[RuCl$_3$(DMSO)$_2$(pyz)].

BACKGROUND OF THE INVENTION

Figure 7A:
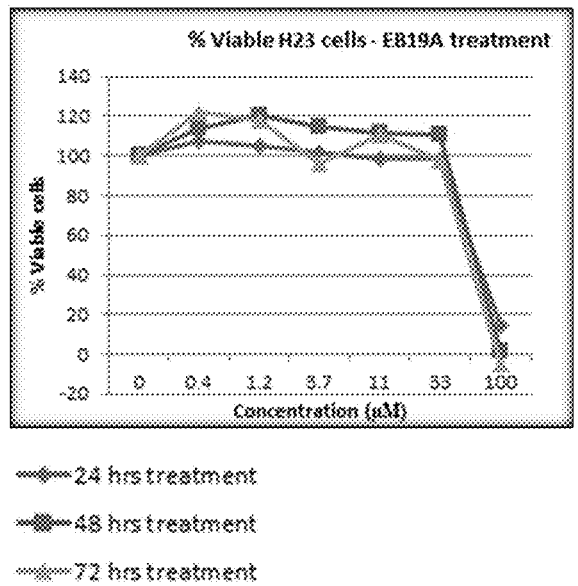
FIG. 7a presents percent viable (National Cancer Institute) NCI-H522 Lung Cancer cell line with mer-[RuCl$_3$(DMSO)(dmpyz)$_2$ drug on different treatment duration.

There have been numerous advancements in the treatment of cancer, leading to the availability of many cancer therapies in the market. Great success has been found through platinum derived anti-cancer drugs. For example, Cisplatin, a chemotherapy medication, is one of the most widely used drugs in clinical use and has shown great promise. Cisplatin is a platinum (Pt) containing chemotherapeutic and considered an essential medicine by the WHO. Cisplatin's clinical success spawned decades-long interest in leveraging transition metals and associated compounds for treatment of human malignancies. However, the effectiveness of this drug, like many of its counterparts, is limited for a variety of reasons. First and foremost, the drug is toxic to human cells and has the propensity to cause severe, unwanted side effects. Additionally, studies have noticed a growing resistance to the drug from some forms of cancer.

While great strides have been made, the field leaves room for additional advancement. The American Cancer Society estimates that over 1,762,000 new cancer cases will be diagnosed in the United States in 2019 alone, and that cancer will cause over 600,000 deaths. Any new cancer treatment is welcomed in the industry as a breakthrough in medical science. But the industry and scientific community are constantly striving to find complexes of transition metals with wider ranges of activities while causing lower systematic toxicities. Any new anti-cancer treatment that also reduces the unwanted side effects and toxicity would be a windfall.

Ruthenium (Ru) based compounds have received interest in recent years, due in part to their improved ability to specifically target cancerous tissue while sparing healthy tissue. Ru compounds are known to impart their anticancer effect largely through genotoxic (e.g, DNA damage, topoisomerase inhibition, etc) activity. This can be problematic as it is often difficult to fully localize treatment to cancerous cells only. Thus, the community is attempting to develop complexes that can more specifically target cancer subtypes, further reducing undesirable damage to healthy cells. One such treatment is disclosed herein that employs Ruthenium (III) complexes.

BRIEF SUMMARY OF THE INVENTION

Disclosed herein is a method of treating cancer through the proper dosing of a neutral ruthenium (III)-pyrazole complex. More specifically, the invention relates to the treatment of certain types of cancer with dosage of complexes of ruthentium (III) reacted with pyrazoles to as to obtain the desired complex.

In one or more embodiments, the complex is a Ruthenium pyrazole selected from the group comprising [RuCl$_3$(DMSO-S)(pyz)$_2$], [RuCl$_3$(DMSO-S) (DMSO-O)(pyz)], [RuCl$_3$(bpy)(dm pyz)], and [RuCl$_3$(DMSO-S)(dm pyz)$_2$]. In a preferred embodiment, the complex is RuCl$_3$(DMSO)(dmPyz)$_2$. As used herein, pyz is pyrazole; DMSO is Dimethylsulfoxide, dmpyz is 3,5-dim ethylpyrazole, and bpy is 2,2'-bipyridine.

DETAILED DESCRIPTION

The subject matter of the present invention is described with specificity herein to meet statutory requirements. However, the description itself is not intended to necessarily limit the scope of claims. Rather, the claimed subject matter might be embodied in other ways to include different steps or combinations of steps similar to the ones described in this document, in conjunction with other present or future technologies.

Furthermore, the described features, structures, or characteristics may be combined in any suitable manner in one or more embodiments. In the following description, numerous specific details are provided, such as examples of dosages, dosage means, amounts of dosage(s), and application times.

Turning first to the complex itself, FIG. 1 shows the Ortep diagram of a particular Ruthenium (III) pyrazole complex, mer—RuCl$_3$(DMSO)(dmPyz)$_2$. As more fully explained in *Synthesis, characterization, and anticancer activity of rutheneium-pyrazole complexes*, Journal of Inorganic Biochemistry 111 (2012) 33-39, which is incorporated herein by reference, this complex may crystallizes in the monoclinic space group Cc that adopts a distorted octahedral geometry with meridional arrangement. Both pyrazole ligands are coordinated to ruthenium through the tertiary ring nitrogen atom N2 as depicted in FIG. 2, The average Ru—Cl bond length, 2.344(9) Å is comparable to other related Ru(III) complexes. The Ru—S bond distance, 2.2783 is appreciably shorter than the average value of 2.34(1) Å found for the Ru(III)-S compounds trans to DMSO-S in the precursor. Likewise the average bond length of Ru—N, 2.089 Å is comparable to Ru(III)-N (imidazole), 2.079 Å. The bond angles of N1Ru1S1, 178.57(11)°; and Cl2Ru1N3, 176.78 (9°) are slightly smaller than the known values of octahedral complexes of ruthenium (III).

Synthesis. The complex may be formed by the displacement of two DMSO ligands from the precursor, mer-[RuCl$_3$(DMSO-S)$_2$(DMSO-0) with pyrazole. A solution of mer-[RuCl$_3$(DMSO-S)$_2$(DMSO-0)](0.2 g, 0.45 mmol) and 3,5-dimethylpyrazole (0.334 g, 3.48 mmol) in dichloromethane (15 mL) was heated to reflux for 9 hours. The brown solution was evaporated to 3 mL and then 1 mL of hexane was added. On cooling at 4° C., a reddish-orange solid was separated (yield 0.262 mmol, 58%). The product was purified by column chromatography with ethyl acetate and hexane (40/60) as eluent. Anal. Calcd. C12H20Cl$_3$N$_4$ORuS·H$_2$O (495.83): C, 29.06; H, 4.95, N, 11.35. Found: C, 29.18.; H, 5.24; N, 10.95. Selected IR absorption bands in KBr (cm−1): v SO1086 (S-DMSO), v C=C (pyz) 1632, v C=N (pyz) 1398. UV-vis (H$_2$O): 362 nm (ε=12.20 M−1 cm−1).

RuCl$_3$(DMSO)(dmPyz)$_2$ was crystallized in the monoclinic space group P2$_1$/n. The X-ray structure in FIG. 2 shows a distorted octahedral geometry (FIG. 1) with three chlorine atoms in a mer configuration. The average Ru—Cl bond length, 2.3411(9). The Ru—S bond distance, 2.3050(9) Å is shorter than the average value of 2.34(1) Å found for the Ru(III)-S corn pounds trans to DMSO-S in the precursor. The average bond length of Ru—N, 2.1005(3) Å, is longer than Ru(III)-N(imidazole), 2.079 Å, and the average bond length (Ru—N) of 1 (2.089 Å). The bond angles of N1Ru1 S1, 176.62(9°) and N1RuCl2, 176.83(3°) are close to the known values of octahedral complexes of ruthenium (III).

TABLE 1

| bond length and bond angle | | | |
|---|---|---|---|
| Ru1-N1 | 2.095(3) | N1-Ru1-N3 | 88.81(12) |
| Ru1-N3 | 2.106(3) | N1-Ru1-S1 | 92.28(9) |
| Ru1-S1 | 2.3050(9) | N3-Ru1-S1 | 176.62(9) |
| Ru1-Cl1 | 2.3356(9) | N1-Ru1-Cl1 | 91.14(9) |
| Ru1-Cl2 | 2.3466(9) | N3-Ru1-Cl1 | 91.36(9) |
| Ru1-Cl3 | 2.3411(9) | N3-Ru1-Cl3 | 90.11(9) |
| | | Cl3-Ru1-Cl1 | 178.38(3) |
| | | N1-Ru1-Cl2 | 176.83(9) |
| | | Cl3-Ru1-Cl2 | 89.24(3) |
| | | Cl1-Ru1-Cl2 | 90.13(3) |

As discussed in the Journal of Inorganic Biochemistry 2012 article supra, it was previously discovered that certain Ru-Pyrazole complexes exhibited specific antibiological activity in the MCF7 (ER$^+$PR$^+$) breast cancer cells. However, it was not shown, or even envisioned, that the currently discussed Ruthenium (III) complex would exhibit any anticancer attributes in subtypes of non-small cell lung cancer (NSCLC). It must be noted that RuCl$_3$(DMSO)(dmPyz)$_2$ does not exhibit general lethality and, therefore, would not ordinarily be believe to be an anti-cancer agent.

Still, preliminary tests show promise that dosage of RuCl$_3$(DMSO)(dmPyz)$_2$ is effective against NSCLC subtypes. FIG. 3 is a table showing the results of Ruthenium complex screening conducted to test the efficacy of the current Ruthenium (III) complexes to various cancer subtypes. The test found 97% inhibition of NSCLC with a treatment of 10 micromole (M) purified. This suggests that the IC$_{50}$ for the complex in the H522 cell lines is under 10 μM, allowing smaller doses to be effective.

Examples measuring the effectiveness of mer-[RuCl3 (DMSO)(dmpyz)2 in treating two lines of cancer cells is presented herein. Lung Cancer Cell lines NCI-H522 and NCI-H23 from ATCC were grown in RPMI (growth medium) supplemented with 10% heat inactivated fetal bovine serum (FBS) along with penicillin and streptomycin. All cells were grown at humidified, carbon dioxide enriched atmosphere (+37° C. with 5% CO$_2$).

NCI-H522 cells were seeded at 50,000 cells/well and NCI-H23 at 30,000cells/well in a 96-well microtiter plate in RPMI with 10% FBS. Cells were incubated at humidified atmosphere (+37° C. with 5% CO$_2$) for overnight attachment. A mer-[RuCl$_3$(DMSO)(dmpyz)$_2$ drug along with the positive control drug Doxorubicin were used in following concentrations (100 μM, 33 μM, 11 μM, 3.7 μM, 1.2 μM, 0.4 μM per well of cells) and added in triplicates and incubated for 3 time durations (24 hrs,48 hrs,72 hrs) at humidified atmosphere (37° C. with 5% CO$_2$). Thereafter the cells were treated with 10 μl (final concentration 0.5 mg/ml) 3-(4,5-dimethylthiazol-2-yl)- 2,5-diphenyltetrazolium bromide (MTT, see Cell Proliferation Kit I MTT Roche: Cat No: 11465007001). The microplate were incubated for 4 hours in a humidified atmosphere (+37° C., 5% CO$_2$). Four hours later 100 μl of solubilization solution (from Roche MTT kit) was added into each well. The plate were allowed to stand overnight in the incubator in a humidified atmosphere (+37° C., 5% CO$_2$). The complete solubilization of the purple formazan crystals was check for and measure the absorbance of the samples using a microplate (ELISA) reader. The wavelength was measure for absorbance of the formazan product at 562 nm the reference wavelength used was 630 nm. Percentage viable cells were calculated as below.

% viable cells=(ab of sample-ab of blank/ab control-ab blank) X100

% cytotoxicity or % inhibition=100−% viable cells

The Effective Dose 50 (ED50) was extrapolated from the dose-response graph. The drug concentration that reduced the viability of the cells by 50% (ED50) was determined by plotting data points over a concentration range and calculating values using PRISM program.

Figure 7B:
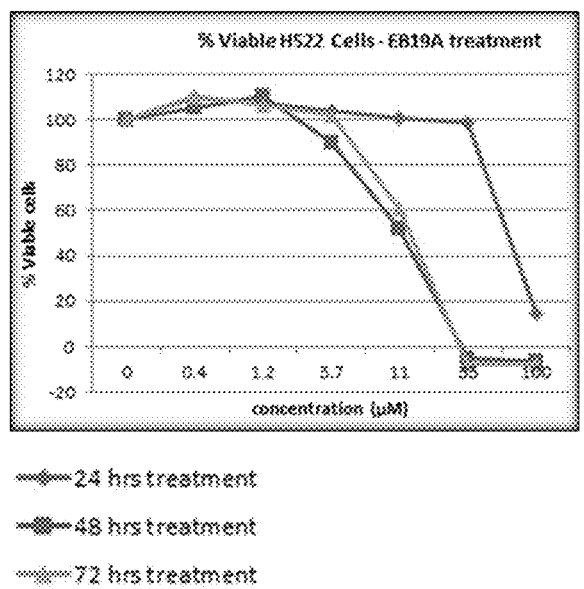
FIG. 7b presents the % viable NCI-H522 and NCI-H23 Lung Cancer cell line with mer-[RuCl$_3$(DMSO)(dmpyz)$_2$ drug on different treatment duration.

The MTT assay is used to measure cellular metabolic activity as an indicator of cell viability, proliferation and cytotoxicity. This colorimetric assay is based on the reduction of a yellow tetrazolium salt (3-(4,5-dimethylthiazol-2-yl)-2,5-diphenyltetrazolium bromide or MTT) to purple formazan crystals by metabolically active cells. Viable cells produce enzymes that convert yellow MTT to insoluble purple formazan. The more viable cells present in a sample, the more intense the purple color. This test is widely used in the in vitro evaluation of cytotoxic potency of drugs. In the present study we applied the MTT assay to evaluate the potency of mer-[RuC$_3$(DMSO)(dmpyz)$_2$ anti-cancer drug in various human lung cancer cell lines. The percent viable NCI-H23 and NCI-H522 cells during different treatment time is shown in FIGS. 7a and 7b. In NCI-H522 cells treated with mer-[RuCl$_3$(DMSO)(dmpyz)$_2$, the cell viability reduces to zero when the drug concentration is 33 μM or more while in NCI-H23 the cell viability reduces to zero when the drug concentration is 100 μM.

Figure 8A:
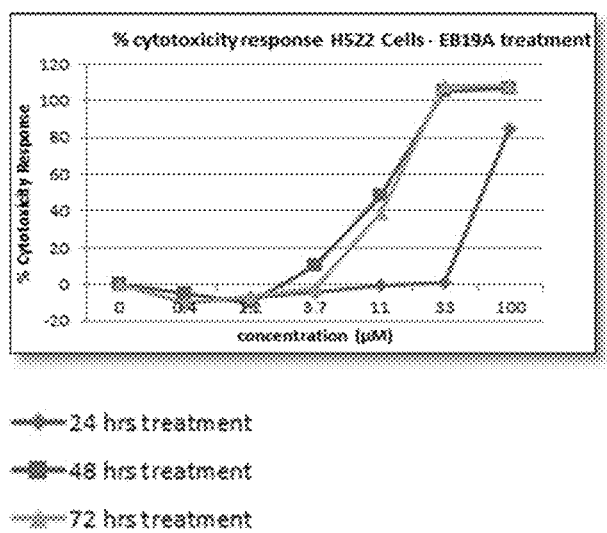
FIG. 8a presents the % cytotoxic response for mer-[RuCl$_3$(DMSO)(dmpyz)$_2$ drug on NCI-H522 Lung Cancer cell line with different treatment duration.
Figure 8B:
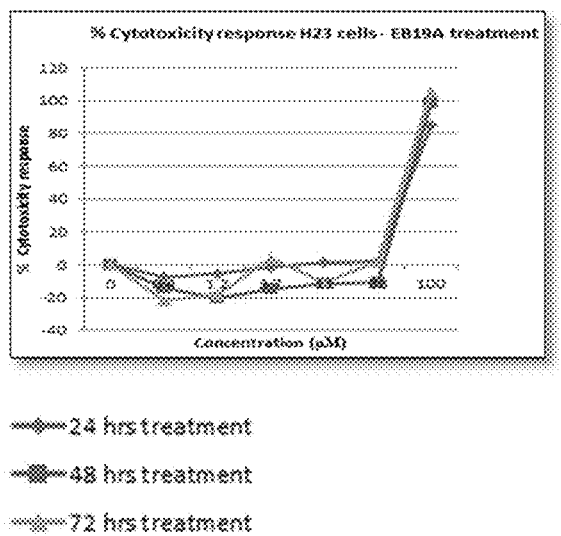
FIG. 8b presents the % cytotoxic response for mer-[RuCl$_3$(DMSO)(dmpyz)$_2$ drug on NCI-H23 Lung Cancer cell line with different treatment duration.

The cytotoxic response of the difference cell lines to mer-[RuCl$_3$(DMSO)(dmpyz)$_2$ drug treatment is shown in FIGS. 8a and 8b. The mer-[RuCl$_3$(DMSO)(dmpyz)$_2$ is highly toxic to the H522 cell lines at 33 μM concentration while is highly toxic to H23 cell lines at 100 μM concentration. The Effective Dose 50 of the drug for the different cell line at different treatment duration is shown in Table 1.

In vitro mer-[RuCl$_3$(DMSO)(dmpyz)$_2$ drug efficacy was tested by cell proliferation assay. Epithelial cytotoxicity MTT assay was established with NCI-H23 and NCI-H522 with doxorubicin as a positive control with ED50 comparable to published data. Optimal time point for testing in this system is 48 hours (or longer). mer-[RuCl$_3$(DMSO)(dmpyz)$_2$ showed modest micromolar ED50 for H522 and H23 cell lines.

It is also envisioned that other Ruthenium complexes may be viable anticancer agents. Representative examples of such complexes are shown in FIGS. 4-6 and include [RuCl$_3$(DMSO-S)(pyz)$_2$], [RuCl$_3$(DMSO-S) (DMSO-O)(pyz)], and [RuCl$_3$(bpy)(dm pyz)].

Reference throughout this specification to features, advantages, or similar language does not imply that all of the features and advantages that may be realized should be or are in any single embodiment. Rather, language referring to the features and advantages is understood to mean that a specific feature, advantage, or characteristic described in connection with an embodiment is included in at least one embodiment. Thus, discussion of the features and advantages, and similar language, throughout this specification may, but do not necessarily, refer to the same embodiment.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change to the basic function to which it is related.

TABLE 1

Effective Dose 50 ( ED50) values of drug mer-[RuCl$_3$(DMSO)(dmpyz)$_2$ on Lung Cancer cell lines at different treatment duration.

|  | 24 hrs | 48 hrs | 72 hrs |
| --- | --- | --- | --- |
| NCI-H522 | 82.077 μM | 11.70 μM | 12.45 μM |
| NCI-H23 | 81.06 μM | 77.4 μM | 59.42 μM |

The invention claimed is:

1. A method of treating a cancer patient comprising administering at least one dose of [RuCl$_3$(dimethylsulfoxide)(3,5-dimethylpyrazole)$_2$] to the cancer patient, wherein the cancer patient has a non-small cell lung cancer subtype.

2. The method of claim 1, wherein the non-small cell lung cancer subtype is adenocarcinoma.

3. The method of claim 1, wherein the at least one dose comprises between 0.1 and 10 μM of [RuCl$_3$(dimethylsulfoxide)(3,5-dimethylpyrazole)$_2$].

* * * * *